United States Patent [19]

Wagner et al.

[11] 4,105,791

[45] Aug. 8, 1978

[54] HYPOLIPIDEMIC CYCLOALKYLAMINOBENZOIC ACIDS

[75] Inventors: Eugene R. Wagner; Donald P. Matthews, both of Midland, Mich.

[73] Assignee: The Dow Chemical Company, Midland, Mich.

[21] Appl. No.: 668,887

[22] Filed: Mar. 22, 1976

[51] Int. Cl.² ............... A61K 31/245; C07C 101/60; C07C 101/62
[52] U.S. Cl. .................. 424/310; 260/448 R; 260/501.1; 260/518 R; 424/316; 424/317; 560/43
[58] Field of Search ............ 260/518 R, 501.1, 471 R; 424/317, 316, 310

[56] References Cited

U.S. PATENT DOCUMENTS

| 3,868,416 | 2/1975 | Albright et al. ............... 260/518 R |
| 3,907,879 | 11/1975 | Murakami et al. ............. 260/518 R |

FOREIGN PATENT DOCUMENTS

| 331,982 | 9/1958 | Switzerland ..................... 260/518 R |
| 897,162 | 5/1962 | United Kingdom .............. 260/518 R |

*Primary Examiner*—Bernard Helfin
*Assistant Examiner*—G. T. Breitenstein
*Attorney, Agent, or Firm*—James W. Ambrosius

[57] ABSTRACT

The present invention relates to novel monocyclic and polycyclic p-cycloalkylaminobenzoic acids, the corresponding pharmaceutically-acceptable salts and the esters thereof. This invention also relates to methods for reducing plasma lipid levels, especially cholesterol and triglyceride levels, using the compounds of the present invention.

30 Claims, No Drawings

HYPOLIPIDEMIC CYCLOALKYLAMINOBENZOIC ACIDS

BACKGROUND OF THE INVENTION

As established by various studies, it is recognized that cholesterol and triglycerides play a major role in the formation of artherosclerotic plaques by accelerating the deposition of blood lipids in the arterial wall.

Very few hypolipidemic benzoic acids have been reported until recently. The most important hypolipidemic derivatives of benzoic acid disclosed to date is tibric acid. U.S. Pat. No. 3,843,662 and U.S. Pat. No. 3,855,255; see also Ryan et al. *Clinc. Pharmacol. Therap.*, 15,218 (1974). There have been two reports of hypolipidemic activity in p-amino benzoic acid analogs. Ger. Offen. No. 2,316,914 (CA82:43070h) and Belgian Pat. No. 815,703. A number of patents have issued describing hydroxy and thio benzoic acid derivatives as hypolipidemics or for use in the treatment for heart disease. Japanese Pat. No. 7,333,742; Japanese Pat. No. 7,333,743; Ger. Offen. No. 2,311,020 (CA82:16563q); U.S. Pat. No. 3,716,644; U.S. Pat. No. 3,732,295; Japanese Pat. No. 7,368,541 (CA80:59739c); Japanese J4 No. 9,070,942; *J. Pharm. Soc. Jap.* 94 (3) 387–96 (1974); German Offen. No. 1,963,187 (CA75:63401a); Belgian Pat. No. 805,172; *Arznei. Forsch.*, 22 (2) 465–8 (1972); U.S. Pat. No. 3,856,951; and German Offen. No. 2,149,070. Alkylamino benzoic acid derivatives have also been described as hypolipidemic agents. U.S. Pat. No. 3,868,416. In addition, there has been much work with somewhat related compounds having unsaturated bonds for their liquid crystal properties. Japanese Pat. No. J4 9,052,785, British Pat. No. 1,373,609, and Ger. Offen. No. 2,306,738.

Reports in the literature include p-benzylaminobenzoic acid itself. CA51:8720g; 52:18498d; 52:P8539d; 55:5867c; 57:14973e. Reported monosubstituted p-benzylaminobenzoic acids include various amino, nitro, and methoxy substitutions. CA64:60105g; CA65:7001f; CA64:20105g; and Ger. Offen. 716,668 (CA38:2345g). Several simple multi-substituted analogs have also been reported. CA52:16630b; CA48:6444h; and CA75:141136j. The esters of p-cyclohexylaminobenzoic acid are described in U.S. Pat. Nos. 2,714,607 and 2,857,417. See also CA53:5203h. No hypolipidemic activity has been mentioned for any of these compounds.

Other related art includes p(ar, α-dimethylbenzylamino)benzoic acid and a piperonyl derivative. CA38:P2346. A bicyclic derivative has also been reported. CA58:521f. Related compounds are also disclosed in U.S. Pat. Nos. 3,257,191; 3,674,843; 3,674,844 and 3,780,027.

SUMMARY OF THE INVENTION

The present invention relates to novel monocyclic and polycyclic p-cycloalkylaminobenzoic acids, the corresponding pharmaceutically-acceptable salts and the esters thereof. This invention also relates to methods for reducing plasma lipid levels, especially cholesterol and triglyceride levels, using the compounds of the present invention.

The p-cycloalkylaminobenzoic acids and the corresponding esters of the present invention are represented by the general formula:

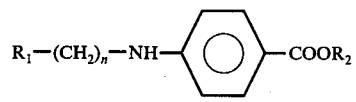

wherein $R_1$ is a monocyclic or polycyclic cycloalkyl radical having from 7 to 10 carbon atoms in the primary ring which may be bridged or unbridged, $R_2$ is hydrogen or a lower alkyl having from 1 to about 3 carbon atoms, and $n$ is an integer of from 0 to 4.

Examples of monocyclic cycloalkyl radicals included in the invention are cycloheptyl, cyclooctyl, cyclononyl, and cyclodecyl. Examples of polycyclic cycloalkyl radicals included in the invention are octahydromethanoindenyl radicals such as 2,3,3a,4,5,6,7,7a-octahydro-4,7-methano-1H-inden-5-yl and tricyclooctanyl radicals such as tricyclo $(3,3,1,1^{3,7})$ octan-3-yl or tricyclo $(3,3,1,1^{3,7})$ octan-2-yl.

As used herein the term octahydromethanoindenyl refers to a radical having the general structure:

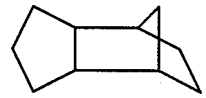

and tricyclooctanyl refers to a radical having the general structure:

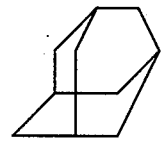

Pharmaceutically-acceptable salts of the p-cycloalkylaminobenzoic acids are considered as being within the scope of this invention. Pharmaceutically-acceptable salts refers to the acid addition salts of those bases which will form a salt with a carboxylic acid and which will not cause an adverse physiological effect when administered to an animal at dosages consistent with good pharmacological activity. Suitable bases thus include, for example, the alkali metal and alkaline earth metal hydroxides, carbonates, bicarbonates, etc., such as sodium hydroxide, potassium hydroxide, calcium hydroxide, potassium carbonate, sodium bicarbonate, magnesium carbonate and the like, ammonia, primary, secondary, and tertiary amines and the like. Also, aluminum salts of the instant compounds may be obtained by treating the corresponding sodium salt with an appropriate aluminum complex such as aluminum chloride hexahydrate, etc.

The compounds of the present invention are crystalline solids which are soluble in many common organic solvents such as, for example, acetone, acetonitrile, or benzene.

Compounds of the present invention have shown hypolipidemic activity in animals and in particular in mammals. Hypolipidemic activity as used herein refers to the effect of lowering the blood lipid content and in particular the cholesterol and triglyceride content of the serum, although not all member compounds will display both hypocholesterolemic and hypotriglyceridemic activity. The compounds of the present invention are therefore suitable for use in treating serum hyperlipidemia in mammals and in particular are useful for treatment of hypercholesterolemia and hypertriglyceridemia, that is, abnormally high levels of lipids, cholesterol, or triglycerides, respectively, in the serum. The compounds can be administered orally or parenterally by subcutaneous, intravenous, or intraperitoneal injection or by implantation or the like, oral administration being preferred.

The hypolipidemic amount of the cycloalkylaminobenzoic acid compounds to be administered to an animal, that is, the amount which is effective to significantly lower the serum lipid level, can vary depending upon such factors as the animal treated, the particular cycloalkylaminobenzoic acid compound employed, the desired lipid level to be obtained, whether or not the animal is hypolipidemic, the period of administration and the method of administration. In general an effective daily dosage range is from about 1 to 400 milligrams per kilogram of body weight, with a daily dosage range of from about 5 mg/kg to 30 mg/kg of body weight being preferred.

For oral administration, pharmaceutical preparations of the p-amino benzoic acids may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonates or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or codliver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan tri-oleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweeting agents, flowing agents, coloring materials and preservatives.

The p-cycloalkylamino benzoic acids can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25-30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

DETAILED DESCRIPTION OF THE INVENTION

The p-cycloalkylaminobenzoic acid compounds that are the subject of the present invention are prepared by known procedures. In general, member compounds are made by reacting p-aminobenzoic acid in an inert solvent with a selected cycloalkyl carboxaldehyde as shown below:

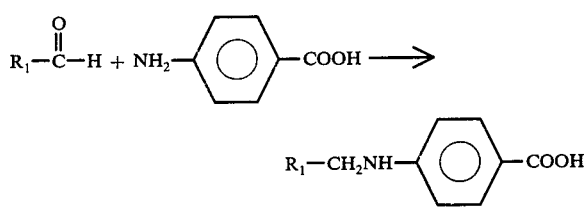

where $R_1$ is a monocyclic or polycyclic cycloalkyl as described hereinabove.

If not commercially available the starting aldehyde may be prepared from the corresponding carboxylic acid by the procedure described in *J. Am. Chem. Soc.*, 92, 5775(1970). The preparation of a starting aldehyde is illustrated in Example 1.

In compounds where n = o, that is where the cycloalkyl group is bonded directly to the amino group without an intervenient methyl group, the corresponding ketone is used to prepare the cycloalkylamino benzoic acid instead of the aldehyde.

EXAMPLE 1

Synthesis of 3-Cycloheptyl carboxaldehyde reactant

Synthesis of 4-[(Cycloheptylmethyl)amino]benzoic acid

Liquid methylamine was added to 35.55 g (0.25 mol) 3-cyclohexylcarboxylic acid with stirring. When about 500 ml had collected, the clear solution was treated with short pieces of lithium wire until 1.77 grams had been added. The reaction product mixture became thick with precipitate. Additional pieces of lithium wire (3.43 g) were added. The resulting reaction was a dark blue-black in color. It was stirred for 4½ hours.

To the reaction mass was carefully added 250 ml saturated ammonium chloride (NH₄Cl) solution. The resulting layers were extracted four times with ether and the combined ether extracts washed three times with 10% hydrochloric acid, once with sodium hydrogen carbonate (NaHCO₃) and twice with water. The so-treated ether extract was dried over sodium sulfate (Na₂SO₄) and the ether removed by evaporation to leave an oil (8.75 g, 0.069 mol). Gas chromatographic analysis showed this product to be 3-cycloheptylcarboxaldehyde of a purity sufficient for use directly in a condensation reaction with p-aminobenzoic acid to yield the corresponding 4-[(cycloheptylmethyl)amino]benzoic acid.

The cycloheptane carboxaldehyde (8.75 g, 0.069 mol) was added dropwise to a refluxing mixture of 17 grams of zinc dust, 9.32 grams (0.068 mol) of p-amino benzoic acid, 17 ml of glacial acetic acid, and 90 ml of benzene. The reaction was refluxed for 3 hours during which period evolved water was collected. The mixture was filtered hot, and the solvent was evaporated. The resulting solid was recrystallized from 200 ml of acetonitrile to give 8.69 grams of brown needles of 4-[(cycloheptylmethyl)amino]benzoic acid. Recrystallization and decolorization from benzene gave 6.25 grams of purified product.

This compound had a melting point of 174°–176° C.

Elemental analysis showed C-72.8%; H-8.35%; N-5.82%. Theoretical analysis for the compound is C-72.84%; H-8.56%; N-5.66%.

EXAMPLE 2

Synthesis of 4-[(Cyclooctylmethyl)amino]benzoic acid

Cyclooctane carboxaldehyde (14.72 g, 0.105 mole) was added dropwise to a stirred and refluxing mixture of 13.7 g (0.1 mole) p-aminobenzoic acid, 25 g zinc dust, 25 ml glacial acetic acid and 125 ml of benzene. Water which evolved was collected in a Dean-Stark trap as the reaction mass was refluxed overnight. Following the reflux period, the resulting product mass was filtered while still hot. Upon cooling the filtrate, crystals formed therein. The benzene was evaporated and the residue recrystallized from acetonitrile. The crude product weighed 18.77 g. It was decolorized and recrystallized from benzene. The resulting purified 4-[(cyclooctylmethyl)amino]benzoic acid product weighed 12.93 g. It had a melting point of 160°–162° C.

Elemental analysis showed C-73.80%; H-8.75%; N-5.53°. Theoretical analysis for the subject compound is C-73.53%; H-8.87%; N-5.36%.

Infrared and NMR analysis confirmed this product structure.

Following the general procedure set forth in the preceding examples a number of other monocyclic p-cycloalkylaminobenzoic acids were prepared having the general formula:

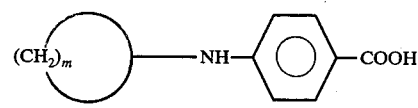

Table I summarizes the results of these studies.

TABLE I

| Ex. No. | m= | Analysis Calculated C | H | N | Analysis Found C | H | N | Empirical Formula | Molecular Weight | Recrystallization Solvent | Melting Point °C |
|---|---|---|---|---|---|---|---|---|---|---|---|
| 3 | 7 | 71.20 | 7.81 | 6.39 | 71.18 | 7.70 | 6.46 | C₁₃H₁₇NO₂ | 219.29 | Hexane | 187–188 |
| 4 | 8 | 72.07 | 8.21 | 6.00 | 72.0 | 8.12 | 5.86 | C₁₄H₁₉NO₂ | 233.31 | Hexane | 153–154 |
| 5 | 10 | 75.21 | 9.63 | 4.67 | 75.5 | 9.51 | 4.59 | C₁₉H₂₉NO₂ | 317.48 | Hexane | 195–197 |

In addition to the monocyclic cycloalkyls described above a number of polycyclic derivatives were also prepared as illustrated by the following examples.

EXAMPLE 6

Synthesis of 4-(octahydro-1H-4,7-methanoindenyl-5-ylamino)benzoic acid

A mixture of 27.4 grams (0.2 mol) of p-aminobenzoic acid, 50 grams of powdered zinc and 50 ml of glacial acetic acid in 250 ml of toluene was stirred and heated to reflux. To this mixture 30 grams (0.2 mol) of 8-keto-tricyclo (5,2,1,0²·⁶)decane was added dropwise. The reaction mass was refluxed with water collection for 6 hours. The hot reaction mixture was filtered, the filtrate evaporated, and the resulting solid dried. The crude 4-(octahydro-1H-4,7-methanoindenyl-5-ylamino)benzoic acid was recrystallized from 1500 ml of toluene to give 22.3 grams of product. The white powder was recrystallized again. The product had a melting point of 223°–225° C. Elemental analysis showed carbon 75.3%, hydrogen 7.65%, and nitrogen 5.29%. Theoretical analysis was carbon 75.25%, hydrogen 7.80%, and nitrogen 5.16%.

Other polycyclic cycloalkylaminobenzoic acids having the general formula

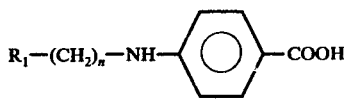

were also prepared and are shown in Table II.

The data indicate that the monocyclic compounds 4-[(cycloheptylmethyl)amino]benzoic acid (compound Example 1) and 4-[(cyclooctylmethyl)amino]benzoic acid (compound Example 2) significantly reduced serum cholesterol and the triglycerides in both the liver and serum while causing only a minimal increase in liver weight. The results obtained with other monocy-

TABLE II

| Ex. No. | $R_1=$ | $n=$ | Analysis Calculated C | H | N | Analysis Found C | H | N | Empirical Formula | Molecular Weight | Recrystallization Solvent | Melting Point °C |
|---|---|---|---|---|---|---|---|---|---|---|---|---|
| 7 | (adamantyl) | 0 | 75.76 | 8.12 | 4.90 | 75.9 | 7.90 | 4.84 | $C_{18}H_{23}NO_2$ | 285.38 | Toluene/Acetone | 259–61 |
| 8 | same | 1 | 75.76 | 8.12 | 4.90 | 75.9 | 8.09 | 5.08 | $C_{18}H_{23}NO_2$ | 285.38 | Toluene/isopropanol | 250–2 |
| 9 | (noradamantyl) | 1 | 75.25 | 7.80 | 5.16 | 75.3 | 7.65 | 5.29 | $C_{17}H_{21}NO_2$ | 271.36 | Toluene | 223–5 |
| 10 | (tricyclooctanyl) | 1 | 75.76 | 8.12 | 4.90 | 75.6 | 8.05 | 5.09 | $C_{18}H_{23}NO_2$ | 285.38 | isopropanol/$H_2O$ | 193–4 |

The hypolipidemic effect of the compounds of the invention is illustratively demonstrated in rats. In this procedure, a compound of the present invention is dissolved in acetone, taken up on a silica gel and mixed with normal ground feed to yield concentrations of 0.125 percent of the compound in the animal feed. The treated feed was administered to male rats weighing 150–160 grams over a fourteen day period. Following the fourteen day feeding period, the rats were sacrificed, and blood samples were collected. The liver was removed, weighed, and frozen for future analysis. The relative levels of serum cholesterol in the blood samples was determined by the Henly method. A. A. Henly, *Analyst*, 82, 286 (1957). Liver cholesterol was measured by the Sperry-Webb method. *Journal of Biological Chemistry* 187, 97 (1950). The relative levels of triglycerides in the blood and liver samples were determined by the Van Handel and Zilversmit method. *J. Lab. Clin. Med.* 50, 152 (1957) and *Clin. Chem.* 7, 249 (1961). Taking the average levels of control rats as standard the mean results obtained in the treated groups is thereby ascertained.

The data presented in Table III summarizes the results of the above studies.

clic compounds while somewhat less dramatic also indicated reduced serum cholesterol or serum triglycerides in the test animals as compared to the controls.

Among the polycyclic compounds 4-(octahydro-1H-4,7-methanoindenyl-5-ylamino)benzoic acid (compound Example 6) showed significant activity while causing only a minimal increase in liver weight. The other polycyclic compounds also showed satisfactory activity in lowering serum cholesterol and serum triglycerides in the test animals.

I claim:

1. A compound of the formula

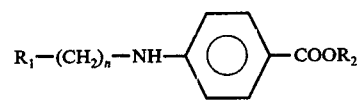

wherein
$R_1$ is a monocyclic cycloalkyl radical having from 7 to 10 carbon atoms or a polycyclic cycloalkyl radical selected from the group consisting of octahydromethanoindenyl and tricyclooctanyl,
$n$ is an integer of from 0 to 4, and

TABLE III

| Compound Example Number | Serum Cholesterol* % Reduction | Serum Triglycerides* % Reduction | Liver Cholesterol* | Liver Triglycerides* | Liver Weight* % Increase |
|---|---|---|---|---|---|
| 1 | −26 | −76 | −3 | −23 | +4 |
| 2 | −26 | −74 | −6 | −22 | +5 |
| 3 | −13 | −43 | — | — | 0 |
| 4 | −8 | −36 | — | — | +23 |
| 5 | −14 | +9 | — | — | +21 |
| 6 | −29 | −71 | −3 | −16 | +5 |
| 7 | −10 | −28 | — | — | +6 |
| 8 | −11 | −43 | — | — | +10 |
| 9 | −4 | −24 | — | — | +2 |
| 10 | −17 | −52 | −5 | −14 | +14 |

*All data represents relative change in values for the treated animals when compared to the control group $R_2$ is a lower alkyl group of from one to about three carbon atoms or hydrogen and further including the pharmaceutically-acceptable salts thereof.

2. The compound of claim 1 wherein $R_1$ is a monocyclic cycloalkyl radical selected from the group consisting of cycloheptyl, cyclooctyl, cyclononyl, and cyclodecyl.

3. The compound of claim 2 wherein $R_1$ is cycloheptyl and $n$ is 1.

4. The compound of claim 3 which is 4-[(cycloheptylmethyl)amino]benzoic acid.

5. The compound of claim 2 wherein $R_1$ is cyclooctyl and $n$ is 1.

6. The compound of claim 5 which is 4-[(cyclooctylmethyl)amino]benzoic acid.

7. The compound of claim 1 wherein $R_1$ is a polycyclic cycloalkyl radical selected from the group consisting of octahydromethanoindenyl and tricyclooctanyl.

8. The compound of claim 7 wherein $R_1$ is an octahydromethanoindenyl having the structure of

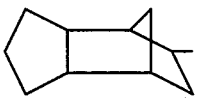

9. The compound of claim 8 which is 4-(octahydro-1H-4,7-methanoindenyl-5-ylamino)benzoic acid.

10. A method for lowering serum lipids in a hyperlipidemic mammal which comprises administering internally to the mammal a hypolipidemically effective amount of a compound having the formula

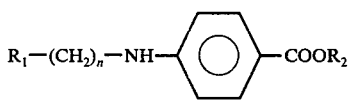

wherein
$R_1$ is a monocyclic cycloalkyl radical having from 7 to 10 carbon atoms or a polycyclic cycloalkyl radical selected from the group consisting of octahydromethanoindenyl and tricyclooctanyl,
$n$ is an integer of from 0 to 4, and
$R_2$ is a lower alkyl group of from one to about three carbon atoms or hydrogen and further including the pharmaceutically-acceptable salts thereof.

11. The method of claim 10 wherein $R_1$ in the compound is a monocyclic cycloalkyl radical selected from the group consisting of cycloheptyl, cyclooctyl, cyclononyl, and cyclodecyl.

12. The method of claim 11 wherein $R_1$ is cycloheptyl and $n$ is 1.

13. The method of claim 7 wherein the compound is 4-[(cycloheptylmethyl)amino]benzoic acid.

14. The method of claim 11 wherein $R_1$ is cyclooctyl and $n$ is 1.

15. The method of claim 14 wherein the compound is 4-[(cyclooctylmethyl)amino]benzoic acid.

16. The method of claim 10 wherein $R_1$ in the compound is a polycyclic cycloalkyl radical selected from the group consisting of octahydromethanoindenyl and tricyclooctanyl.

17. The method of claim 16 wherein $R_1$ is an octahydromethanoindenyl having the structure

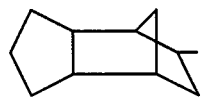

18. The method of claim 17 wherein the compound is 4-(octahydro-1H-4,7-methanoindenyl-5-ylamino)benzoic acid.

19. The method of claim 10 wherein the mammal is hyperlipidemic.

20. The method of claim 19 wherein the mammal is hypercholesterolemic.

21. The method of claim 19 wherein the mammal is hypertriglyceridemic.

22. A hypolipidemic composition comprising a suitable pharmaceutical carrier and a hypolipidemically effective amount of a compound having the formula

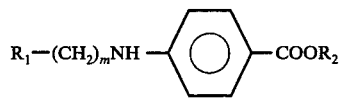

wherein
$R_1$ is a monocyclic cycloalkyl radical having from 7 to 10 carbon atoms or a polycyclic cycloalkyl radical selected from the group consisting of octahydromethanoindenyl and tricyclooctanyl,
$n$ is an integer of from 0 to 4, and
$R_2$ is a lower alkyl group of from one to about three carbon atoms or hydrogen and further including the pharmaceutically-acceptable salts thereof.

23. The composition of claim 22 wherein $R_1$ in the compound is a monocyclic cycloalkyl radical selected from the group consisting of cycloheptyl, cyclooctyl, cyclononyl, and cyclodecyl.

24. The composition of claim 23 wherein $R_1$ is cycloheptyl and $n$ is 1.

25. The composition of claim 24 wherein the compound is 4-((cycloheptylmethyl)amino)benzoic acid.

26. The composition of claim 23 wherein $R_1$ is cyclooctyl and $n$ is 1.

27. The composition of claim 26 wherein the compound is 4-((cyclooctylmethyl)amino)benzoic acid.

28. The composition of claim 22 wherein $R_1$ in the compound is a polycyclic cycloalkyl radical selected from the group consisting of octahydromethanoindenyl and tricyclooctanyl.

29. The composition of claim 28 wherein $R_1$ is octahydromethanoindenyl having the structure

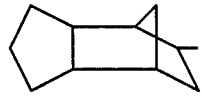

30. The composition of claim 29 wherein the compound is 4-(octahydro-1H-4,7-methanoindenyl-5-ylamino)benzoic acid.

* * * * *